US00PP10892P

United States Patent [19]

Cardona

[11] Patent Number: Plant 10,892

[45] Date of Patent: May 11, 1999

[54] CHRYSANTHEMUM PLANT NAMES 'GOLDEN STATE DAISY'

[75] Inventor: Jose Luis Cardona, Santamartaf, Mexico

[73] Assignee: Clearwater Nursery, Inc., Nipomo, Calif.

[21] Appl. No.: 09/000,918

[22] Filed: Dec. 30, 1997

[51] Int. Cl.[6] ..... A01H 5/00

[52] U.S. Cl. ..... Plt./295

[58] Field of Search ..... Plt./295

*Primary Examiner*—Howard J. Locker

*Attorney, Agent, or Firm*—Arnold, White & Durkee

[57] ABSTRACT

The present invention comprises a new and distinct cultivar of Chrysanthemum, botanically known as *Dendranthema grandiflora*, and referred to by the cultivar name Golden State Daisy is described. The plant is particularly characterized by its golden yellow color and elliptic/spoon shape of its ray florets.

1 Drawing Sheet

BACKGROUND OF THE PLANT

Golden State Daisy was found as a natural daisy from mutation (sport) of the variety Golden State (U.S. Plant Pat. No. 8,694) by Jose Luis Cardona in a controlled environment at Clearwater Nursery, Nipomo, Calif. 93444, U.S.A. This mutation was discovered as one flowering shoot within a flowering bench of seedlings of Golden State, in April of 1993.

The first act of asexual reproduction of Golden State Daisy was accomplished when Jose Luis Cardona took vegetative cuttings in July of 1993, in a controlled environment in Nipomo, Calif.

Horticultural examination of controlled flowerings of successive plantings has shown that the unique combination of characteristics as herein disclosed for Golden State Daisy are firmly fixed and are retained through successive generations of asexual reproduction.

Golden State Daisy has not been observed under all possible environmental conditions. The phenotype may vary significantly with variations in the environment such as temperature, light intensity and day length.

The following observations, measurements and comparisons describe plants grown in a controlled environment in Nipomo, Calif. Unrooted cuttings were directly stuck into 6.4" pots and grown under the natural temperature and day length prevailing in June through August of 1997.

The following traits have been repeatedly observed and are determined to be basic characteristics of Golden State Daisy, which in combination distinguish this Chrysanthemum as a new and distinct cultivar.

1. Flat capitulum form.
2. Flat capilulum type.
3. Yellow fully expanded ray florets.
4. Yellow Daisy disc with green eye.
5. Diameter across the face of the capitulum is 8.5 cm.
6. Exceptional uprignt to spreading habit when an average of 5 breaks after a single pinch.
7. Flowering response is approximately 59 days from the start of short days.
8. Relatively easy to control plant height from bench such that the finished height will range from 16 inches to 18 18 inches depending on pot size and market requirements.

Golden State Daisy differs from its parent, Golden State (U.S. Plant Pat. No. 8,694), in the following ways.

1. The flower in Golden State Daisy has a traditional daisy eye; i.e., the disc florets do not dramatically increase in length as the disc matures. In contrast, the eye of the Golden State flower is that of a true anemone, having disc florets that significantly increase in length as the flower matures.

Golden State Daisy differs from Golden State's parents Indo (U.S. Plant Pat. No. 6,774) and Hopscotch (U.S. Plant Pat. No. 5,816) in the following ways.

1. Golden State Daisy has an 8.5 week response time, while Indo and Hopscotch have an 8 week response time.
2. Indio is an anemone rather than a daisy and is shorter than Golden State Daisy
3. There are no known foliage sensitivities with Golden State Daisy (nor Golden State while Indio has known sensitivity to the chemical pesticide. Dursban.
4. Hopscotch is not recommended for year round production, while this not not a problem for Golden State Daisy.

DESCRIPTION OF PHOTOGRAPH

The accompanying photographic drawing show a typical inflorescence and leaf characteristics of Golden State Daisy, with the colors being as rearly true as possible with illustrations of this type. The photograph shows Golden State Daisy grown as a pinched spray pot mum with 5 cuttings in a 6.5" pot.

DESCRIPTION OF PLANT

Of the commercial cultivar known to the inventor, in addition to Golden State, the most similar in form, color, and habit to Golden State Daisy are the cultivars Miramar (U.S. Plant No. 7,469) and Yellow Blush (U.S. Plant Pat. No. 9,455). Reference is made to the attached "Chart A" which compares certain characteristics of Golden State Daisy to the same characteristics of the above mentioned cultivars. The plants were grown side by side in a controlled greenhouse environment. Growth regulator B-Nine™ was applied at 2,500 ppm in 3 applications. Comparisons were made in 1997 in Nipomo, Calif.

CHART A

| CHARACTERISTIC | YELLOW BLUSH | GOLDEN STATE DAISY | MIRAMAR |
|---|---|---|---|
| Capitulum Form | Flat | Flat | Flat |
| Capitulum Type | Daisy | Daisy | Daisy |

CHART A-continued

| CHARACTERISTIC | YELLOW BLUSH | GOLDEN STATE DAISY | MIRAMAR |
|---|---|---|---|
| Diameter Across Face of the Capitulum | 8.5 cm | 8.5 cm | 8.7 cm |
| Diameter of Disc | 1.8 cm | 1.7 cm | 1.9 cm |
| Branching Pattern | Upright and Spreading | Upright and Spreading | Upright and Spreading |
| Breaks/Pinch | 5 | 5 | 4 |
| Height in a 6.5" Pot | 16–18" | 16–18" | 16–18" |
| Disc Floret | Edge Begin w/9A Graduating to Yellow Green 144A | Edge Begin w/9A Graduating to Yellow Green 144A | Edge Begin w/9A Graduating to Yellow Green 144A |
| # Disc Florets | 190 | 243 | 348 |
| Length of Disc Florets | 0.5 cm | 0.6 cm | 0.5 cm |
| Ray Floret Color | Front: Golden Yellow: 5A Back: Pale Yellow: 5B | Front: Golden Yellow: 9A Back: Pale Yellow: 8A | Front: Golden Yellow: 5A Back: Pale Yellow: 5C |
| # Ray Florets | 27.66 | 21 | 49 |
| Shape of Ray Florets | Elliptic | Elliptic/Spoon | Elliptic |
| Length of Ray Florets | 4.1 cm | 4.2 cm | 4.0 cm |
| Width of Ray Florets | 1.5 cm | 1.5 cm | 1.1 cm |
| Number of Flowers/Break | 8 | 7 | 7.2 |
| Leaf Color | Front: 147A Back: 147B | Front: 147A Back: 147B | Front: 147A Back: 147B |
| Mature Leaf Width | 5.6 cm | 6.6 cm | 6.1 cm |
| Mature Leaf Length | 9.6 cm | 10.8 cm | 10.9 cm |
| Response/ Treatment | 8 wk medium vigorous grower | 8.5 wk medium vigorous grower | 9 wk medium vigorous grower |

Similar traits of these cultivars include the flat, daisy capitulum. The diameter of the capitulum of Golden State Daisy is maller than the capitulum of Miramar. Both cultivars have similar upright, spreading branching patterns. Golden State Daisy has equal breaks per pinch to Yellow Blush but a greater number than Miramar. The finished plant height is similar for each cultivar, as is the disc floret color. Golden State Daisy tends to have more disc florets than Yellow Blush, while its tends to have fewer disc florets than Miramar. The length of the disc florets is greater for Golden State Daisy in comparison in both Yellow Blush and Miramar.

Using The Royal Horticultural Society Colour Chart as a standard reference, the front ray floret color for Golden State Daisy is golden yellow 9-A while the color of the front ary florets of Yellow Blush and Miramar are golden yellow 5-A. Golden State Daisy has fewer ray florets than Yellow Blush and Miramar. The ray florets of all three cultivars are elliptic, while Golden State Daisy tends to be slightly spooned from the base of the floret. Golden State Daisy has ray florets that are longer in the length than Yellow Blush and Miramar. The widths of the ray florets of Golden State Daisy are the same for Yellow Blush. However, Golden State Daisy has wider ray florets than Miramar. The three varieties have the same leaf color. Golden State Daisy has longer mature leaves than Yellow Blush, yet has slightly shorter leaves than Miramar. The response time of these varieties from the start of short days is unique for each: Yellow Blush (8 WK); Golden State Daisy (8.5 WK); Miramar (9 WK).

Color designations are made with respect to the 1986 edition of R.H.S. Color Chart, first published in 1986 by the British Royal Horticultural Society, London England. The B-Nine™ growth regulator referred to in the culturing procedures is 2,2-dimethylhydrazide sold under the name of Daminozide or Alar, manufactured by UniRoyal.

THE PLANT

Origin: Naturally occurring mutation of Golden State.

Classification:

*Botanical.*—Dendranthema grandiflora.

*Common name.*—Chrysanthemum.

*Cultivar name.*—Golden State Daisy.

*Commercial.*—Flat daisy to be grown primarily as a Spray/CBR (center bud removed) pot mum. As a Standard/CBR, the flower exhibits a strong spooning habit or novelty form of pot mum.

Asexual reproduction:

*Cutting type.*—URC (unrooted cutting).

*Rooting habit.*—Dense, prolific.

Inflorescence:

*Capitulum.*—Form: Flat. Type: Daisy. Diameter across face: 8.5 cm (average).

*Corolla of ray florets.*—Color (general tonality from a distance of three meters): Front Fully Expanded Ray Floret: 9A. Back Fully Expanded Ray Floret:8A. Disc Floret Color. Edge begins with 9A to Center Green of 144B.

*Reproductive organs.*—Androecium: Absent. Gynocecium: Present in both ray and disc florets. Pollen: Absent.

General appearance:

*Height.*—When grown in a 6.5" pot with 1–4 applications of B-Nine™, the total plant height from the bottom of the pot may be maintained at 16 to 18 inches.

*Branching pattern.*—Upright and spreading with an average of 5 breaks when grown with one pinch.

*Foliage.*—Color (upper surface): 147A. Color (lower surface) 147B. Shape: Lobed and serrated (see photograph). Leaf wideth: 6.6 cm. Leaf length 10.8 cm.

What is claimed is:

1. A new and distinct Chrysanthemum plant substantially as herein described and shown.

* * * * *

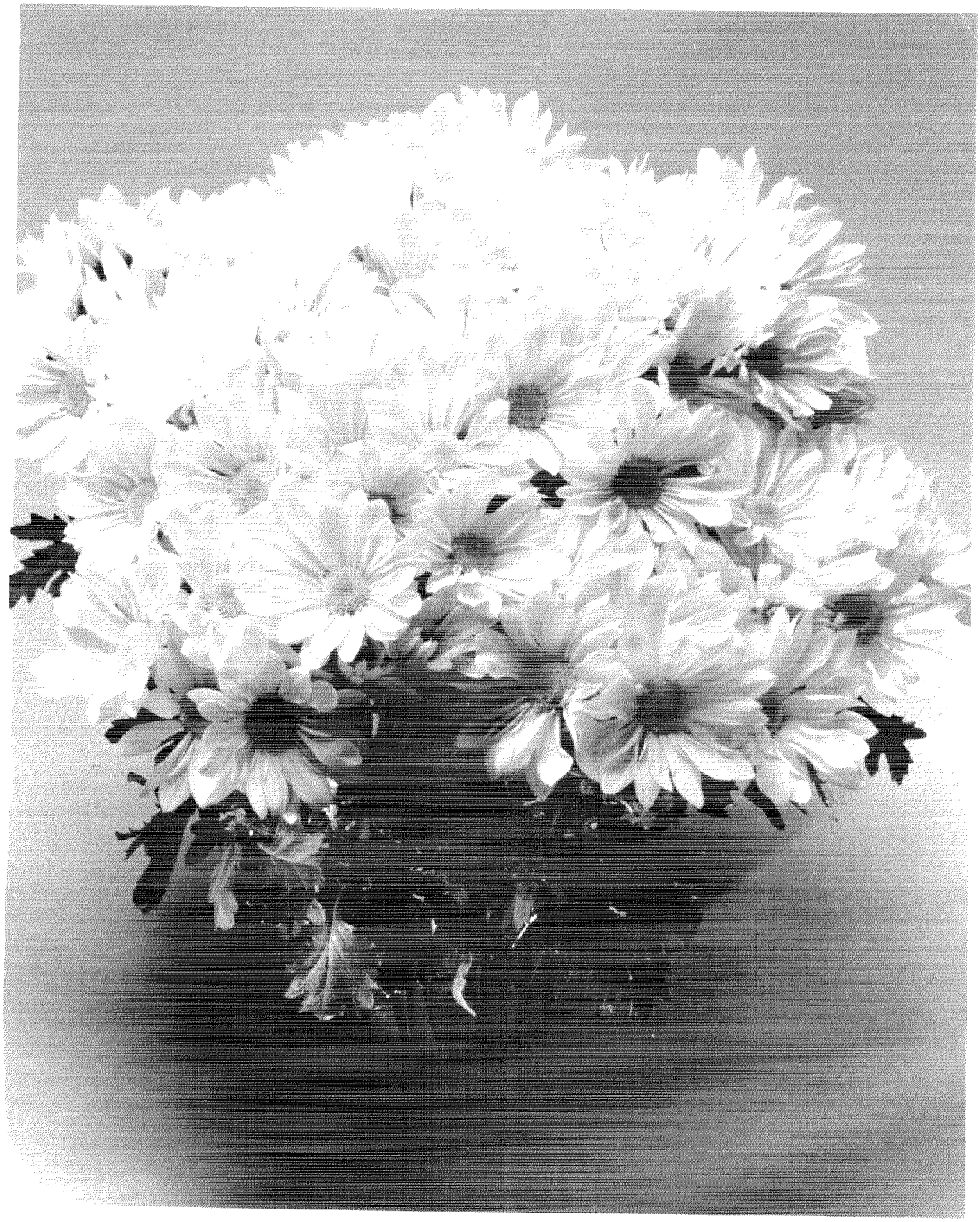

UNITED STATES PATENT AND TRADEMARK OFFICE

CERTIFICATE OF CORRECTION

PATENT NO. : Plant 10,892

DATED : May 11, 1999

INVENTOR(S) : Jose Luis Cardona

It is certified that error appears in the above-identified patent and that said Letters Patent is hereby corrected as shown below:

On the title page:

In the Title, delete [NAMES] and substitute therefore --NAMED--.

Item [75] delete "Santamartaf, Mexico" and insert --Santa Maria, CA-- therefore

Signed and Sealed this

Twenty-sixth Day of October, 1999

*Attest:*

Q. TODD DICKINSON

*Attesting Officer*

*Acting Commissioner of Patents and Trademarks*